US008465481B2

(12) United States Patent
Mazzone et al.

(10) Patent No.: US 8,465,481 B2
(45) Date of Patent: Jun. 18, 2013

(54) PROVIDING CRYOTHERAPY WITH A BALLOON CATHETER HAVING A NON-UNIFORM THERMAL PROFILE

(75) Inventors: James Mazzone, San Jose, CA (US); David Lawrence, San Jose, CA (US); Robert Bencini, Sunnyvale, CA (US); Frank Ingle, Palo Alto, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 796 days.

(21) Appl. No.: 12/580,572

(22) Filed: Oct. 16, 2009

(65) Prior Publication Data
US 2010/0100087 A1 Apr. 22, 2010

Related U.S. Application Data

(60) Provisional application No. 61/106,856, filed on Oct. 20, 2008.

(51) Int. Cl.
*A61B 18/02* (2006.01)

(52) U.S. Cl.
USPC .................................. 606/21; 606/20; 606/26

(58) Field of Classification Search
USPC ...................................................... 606/20–26
See application file for complete search history.

(56) References Cited

U.S. PATENT DOCUMENTS

| | | |
|---|---|---|
| 4,315,512 A | 2/1982 | Fogarty |
| 5,209,727 A | 5/1993 | Radisch |
| 5,400,602 A * | 3/1995 | Chang et al. ................... 62/50.7 |
| 5,423,755 A | 6/1995 | Kesten et al. |
| 6,042,559 A * | 3/2000 | Dobak, III ........................ 604/7 |
| 6,355,029 B1 * | 3/2002 | Joye et al. ........................ 606/21 |
| 6,726,654 B2 * | 4/2004 | Rosenman .................... 604/113 |
| 6,733,439 B2 | 5/2004 | Zigler |
| 6,811,550 B2 * | 11/2004 | Holland et al. ................. 606/21 |

(Continued)

FOREIGN PATENT DOCUMENTS

| | | |
|---|---|---|
| EP | 0724891 A1 | 8/1996 |
| EP | 0850660 A1 | 1/1998 |

(Continued)

OTHER PUBLICATIONS

Authorized office Wolfgang Urack, International Search Report/Written Opinion in PCT/US2009/57452 mailed Nov. 25, 2009, 15 pages.

(Continued)

*Primary Examiner* — Linda Dvorak
*Assistant Examiner* — Amanda Scott
(74) *Attorney, Agent, or Firm* — Seager, Tufte & Wickhem, LLC

(57) ABSTRACT

A cryotherapy catheter can include an elongate member and an inflatable balloon portion at a distal end of the elongate member. The inflatable balloon portion can have an external surface and an interior chamber, and the external surface can include a cooling region and a thermally insulated region. The interior chamber can be configured to receive during a cryotherapy procedure a cryogenic agent for extracting heat from body tissue that is in contact with the cooling region. A thermal profiling component can be disposed in the interior chamber and configured to thermally insulate the thermally insulated region from the cryogenic agent to minimize heat extraction by the cryogenic agent from body tissue that is in contact with the thermally insulated region.

6 Claims, 7 Drawing Sheets

U.S. PATENT DOCUMENTS

| | | | |
|---|---|---|---|
| 6,929,639 B2 | 8/2005 | Lafontaine | |
| 6,936,045 B2 * | 8/2005 | Yu et al. | 606/23 |
| 6,989,009 B2 | 1/2006 | Lafontaine | |
| 7,022,120 B2 | 4/2006 | Lafontaine | |
| 7,172,589 B2 | 2/2007 | Lafontaine | |
| 7,189,227 B2 | 3/2007 | Lafontaine | |
| 7,220,257 B1 | 5/2007 | Lafontaine | |
| 2003/0055415 A1 * | 3/2003 | Yu et al. | 606/21 |
| 2004/0243118 A1 | 12/2004 | Ayers et al. | |
| 2005/0165388 A1 * | 7/2005 | Bhola | 606/14 |
| 2005/0177147 A1 | 8/2005 | Vancelette et al. | |
| 2006/0095066 A1 | 5/2006 | Chang et al. | |
| 2008/0300584 A1 | 12/2008 | Lentz et al. | |
| 2009/0299356 A1 | 12/2009 | Watson | |
| 2010/0076402 A1 | 3/2010 | Mazzone et al. | |
| 2010/0179526 A1 | 7/2010 | Lawrence | |
| 2010/0179527 A1 | 7/2010 | Watson et al. | |

FOREIGN PATENT DOCUMENTS

| | | |
|---|---|---|
| EP | 1120129 A1 | 8/2001 |
| GB | 1288033 A | 9/1972 |
| JP | 2001238953 A | 9/2001 |
| WO | 0207625 A2 | 1/2002 |
| WO | 2008000066 A1 | 1/2008 |
| WO | 2009009472 A1 | 1/2009 |
| WO | 2009146372 | 12/2009 |
| WO | 2010033785 | 3/2010 |

OTHER PUBLICATIONS

International Search Report & Written Opinion for Application No. PCT/US2009/045481, dated Aug. 3, 2009, 20 pages.

* cited by examiner

PROVIDING CRYOTHERAPY WITH A BALLOON CATHETER HAVING A NON-UNIFORM THERMAL PROFILE

CROSS-REFERENCE TO RELATED APPLICATIONS

This application claims priority under 35 U.S.C. §119(e) to U.S. Provisional Patent Application Ser. No. 61/106,856, filed on Oct. 20, 2008, the entire contents of which are hereby incorporated by reference.

BACKGROUND

Atrial fibrillation is a condition that results from abnormal electrical activity within the heart. This abnormal electrical activity may originate from various focal centers of the heart, and the electrical activity generally decreases the efficiency with which the heart pumps blood. It is believed that some of the focal centers reside in the pulmonary veins of the left atrium. It is further believed that atrial fibrillation can be reduced or controlled by structurally altering or ablating the tissue at or near the focal centers of the abnormal electrical activity to form a "conduction block."

One method of structurally altering tissue of the heart and pulmonary veins is to make, for example during open-heart surgery, a series of incisions in a maze-like pattern in the atria, and sew the incisions back together. As the incisions heal, scar tissue forms, and the scar tissue may block the conductive pathways thought to cause atrial fibrillation. The procedure, which was developed under the direction of Dr. James Cox and refined over a period of years, may be referred to as a "maze" procedure, a "Cox maze" procedure, a "Cox maze III" procedure; or the procedure may be referred to by various other names.

A less invasive method of structurally altering tissue of the heart and pulmonary veins involves ablating tissue through the use of an ablation catheter. One example type of ablation catheter delivers radio frequency (RF) energy to ablate tissue; another example ablation catheter ablates tissue with a heat source; another example ablation catheter delivers cryotherapy to ablate tissue by freezing it.

Cryotherapy may be delivered to an appropriate treatment site inside a patient's heart or circulatory system with a cryotherapy catheter. A cryotherapy catheter generally includes a treatment member at its distal end, such as an inflatable balloon having a cooling chamber inside. To deliver the cryotherapy, the inflatable balloon may be introduced at a treatment site inside a patient, and the balloon may be positioned and inflated. Once the balloon is positioned, a cryogenic fluid may be provided by a source external to the patient at the proximal end of the cryotherapy catheter, and delivered distally through a lumen to the cooling chamber, where it may be released. Release of the cryogenic fluid into the chamber can cool the chamber (e.g., through the Joule-Thomson effect), and correspondingly, the balloon's outer surface, which may be in contact with tissue that is to be ablated. Gas resulting from release of the cryogenic fluid may be exhausted proximally through an exhaust lumen to a reservoir or pump external to the patient. As a result of the release of the cryogenic fluid into the chamber and the exhausting of the resulting gas from the chamber, tissue adjacent to the balloon may be cooled to a therapeutic level (e.g., 0° C., −20° C., −60° C., −80° C., or some other appropriate value) for an appropriate period of time.

SUMMARY

When a cryotherapy catheter is employed to deliver cryotherapy to a treatment site internal to a patient, such as to a patient's left or right atrium (e.g., to treat atrial fibrillation), it may be advantageous to focus the cryotherapy on a precise region of tissue to be treated. When a cryo balloon at a distal end of a cryotherapy catheter is employed to deliver the cryotherapy, the cryo balloon can be constructed such that its external surface is thermally insulated from a cryogenic agent internal to the balloon, except for an appropriately sized and shaped cooling region through which the cryotherapy is to be delivered. Other thermally insulated regions of the cryo balloon can protect non-targeted tissue that may be in contact with the balloon during a treatment procedure. In addition, the thermally insulated regions can protect other bodily fluids that may come into contact with the balloon (e.g., blood) from the cooling effect of the balloon.

Cooling regions and thermally insulated regions can be formed in various ways in a cryo balloon. In some implementations, insulation can be disposed between layers of a cryo balloon, or the insulation can be disposed (e.g., laminated) on one or more surfaces of the balloon. Laminations can be configured in particular patterns, and the laminate material itself can be formed in various ways. In some implementations, structures can be included within the cryo balloon to focus the cooling effect on certain cooling regions and away from other thermally insulated regions. In particular, for example, a cryo balloon can include an internal diaphragm that substantially isolates a cryogenic agent to one portion of the balloon (or isolates a cryogenic agent in a particular state, such as a liquid, to the one portion of the balloon). As another example, a cryo balloon can include a lumen that is configured to create eddies in the flow of the cryogenic agent such that the corresponding cooling effect is focused toward one portion of the balloon and away from other portions of the balloon. As another example, a cryo balloon can include multiple nested balloons, and an inner balloon into which cryogenic agent is delivered can be smaller than an outer balloon, such that cooling effect is focused in an area of the outermost balloon that corresponds to the inner balloon.

The details of one or more implementations are set forth in the accompanying drawings and the description below. Other features, objects, and advantages will be apparent from the description and drawings, and from the claims.

DETAILED DESCRIPTION

When a cryotherapy catheter is employed to deliver cryotherapy to a treatment site internal to a patient, such as to a patient's left or right atrium (e.g., to treat atrial fibrillation), it may be advantageous to focus the cryotherapy on a precise region of tissue to be treated. When a cryo balloon at a distal end of a cryotherapy catheter is employed to deliver the cryotherapy, the cryo balloon can be constructed such that its external surface is thermally insulated from a cryogenic agent internal to the balloon, except for an appropriately sized and shaped cooling region through which the cryotherapy is to be delivered. Other thermally insulated regions of the cryo balloon can protect non-targeted tissue that may be in contact with the balloon during a treatment procedure. In addition, the thermally insulated regions can protect other bodily fluids that may come into contact with the balloon (e.g., blood) from the cooling effect of the balloon.

Figure 1:
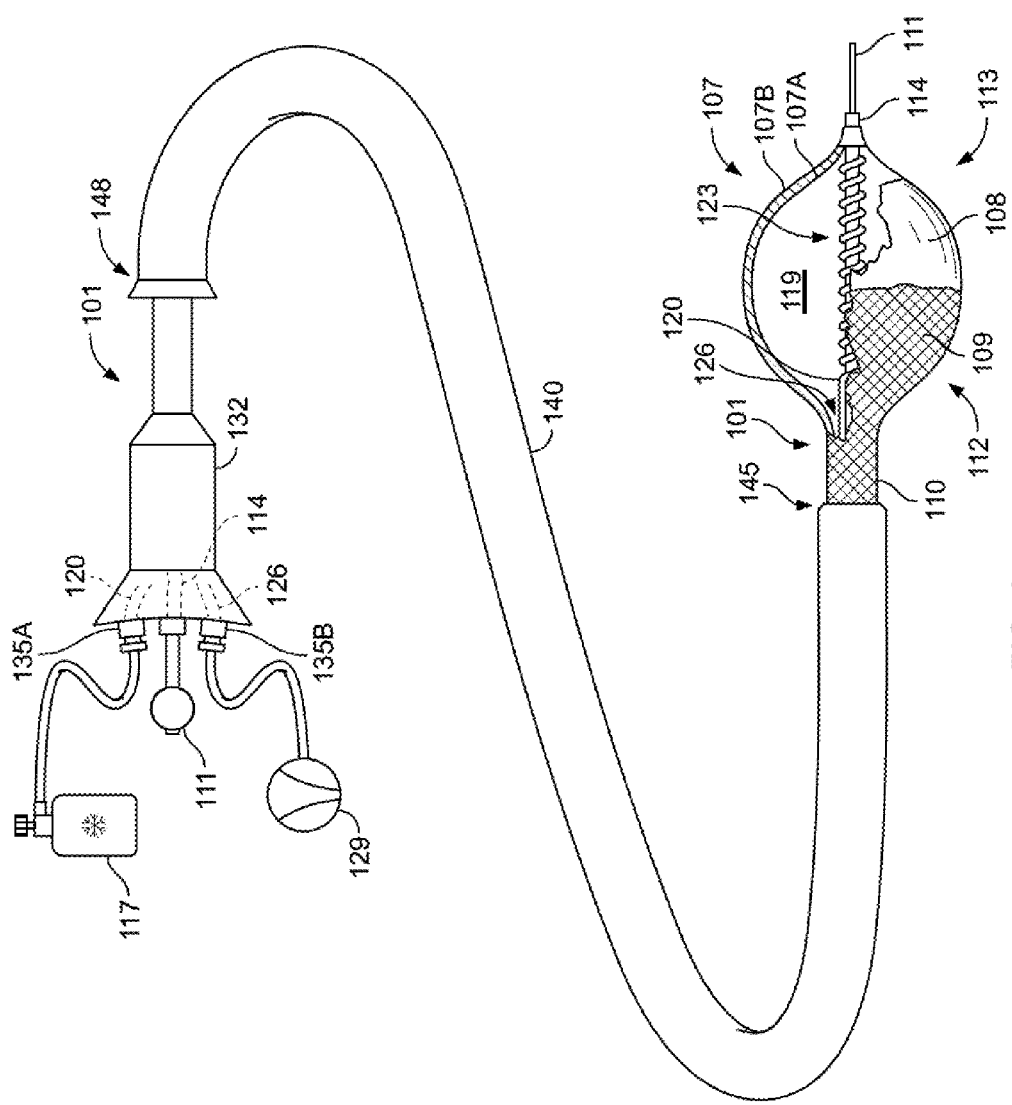
FIG. 1 illustrates an example balloon catheter having a cryo balloon with a cooling region and a thermally insulated region.

FIG. 1 illustrates an example balloon catheter 101 having an inflatable cryo balloon 107 that can be employed to deliver cryotherapy to a treatment site internal to a patient. In particular, the example cryo balloon 107 has at least one cooling region 108 through which the cryotherapy can be delivered (or more precisely, through which heat from adjacent body tissue can be extracted), and at least one thermally insulated region 109 that substantially insulates adjacent body tissue from the cooling effect of a cryogenic agent inside the cryo balloon 107. In some implementations, the cooling region 108 is disposed on a distal portion 113 of the cryo balloon 107, and the thermally insulated region 109 is disposed on a proximal portion 112 of the cryo balloon 107. In other implementations (not shown in FIG. 1), the cooling region includes a pattern (e.g., a linear band, an arc, or a more complex pattern) that can cause tissue adjacent to the pattern to be ablated. In still other implementations (not shown in FIG. 1), the cooling region includes a circumferential band with thermally insulated regions both proximal and distal to the circumferential band. Several examples of different cooling regions and thermally insulating regions are described in more detail below, following a description of additional details of the example cryotherapy catheter 101.

To deliver cryotherapy, the cryotherapy balloon catheter 101 shown in FIG. 1 can be configured to deliver a cryogenic agent (e.g., a cryogenic fluid) from an external source 117 to an interior chamber 119 of the balloon 107, through a supply lumen 120. Inside the interior chamber 119, the cryogenic fluid can be released through a cooling device 123. For example, the cooling device 123 can include a coiled portion of the supply lumen 120 having one or more orifices through which certain cryogenic agents can exit, some of which can undergo a liquid-to-gas phase change that cools the balloon 107 by the Joule-Thomson effect. Gas resulting from the cryogenic fluid being released inside the chamber 119 can be exhausted through a separate exhaust lumen 126. In particular, for example, in some implementations, gas is exhausted through the exhaust lumen 126 to an external vacuum pump 129.

To facilitate coupling the catheter 101 to external equipment, such as the source 117 of a cryogenic agent, or the vacuum pump 129, the catheter 101 can include a port component 132 having a number of coupling members 135A and 135B. The coupling members 135A and 135B can, in some implementations, terminate lumens that are internal to the catheter shaft (e.g., the supply lumen 120 and the exhaust lumen 126) with connectors (e.g., industry-standard medical connectors, proprietary medical connectors, other connectors, etc.) that facilitate connection of the lumens 120 and 126 to the external equipment (e.g., with medical tubing). As shown in FIG. 1, the port component 132 is merely exemplary. Other connections and configurations are possible and contemplated (e.g., connections for pressure sensor(s), electrical sensor(s), multiple vacuum ports, etc.).

In the example of FIG. 1, the balloon catheter 101 is an over-the-wire cryotherapy balloon catheter, having a guidewire 111 disposed inside a guidewire lumen 114. In the implementation depicted, the port component 132 can also provide access to the guidewire lumen 114 and corresponding guidewire 111. In other implementations, the balloon catheter 101 may not employ a guidewire 111.

The cryo balloon 107 can, in some implementations, include two separate balloons 107A and 107B. In some such implementations, the balloons 107A and 107B can inflate and deflate together. The second balloon 107B may function as a safety balloon 107B. That is, in the event that the balloon 107A ruptures or otherwise fails, the safety balloon 107B can prevent agents inside the interior chamber 119 (e.g., cryogenic agents) from directly contacting body tissue internal to the patient and can similarly prevent body tissue and body fluids from reaching the interior chamber 119.

In some implementations, a separate vacuum lumen (not shown) is provided between the balloons 107A and 107B, and can be used to apply a constant vacuum force between the balloons 107A and 107B. In the event that the inner balloon 107A ruptures, the constant vacuum force can continue to evacuate any liquid and/or gas inside the interior chamber 119 and prevent the same from coming into direct contact with tissue internal to the patient. In addition, if either the inner balloon 107A or outer balloon 107B ruptures, a sensor that monitors the vacuum force between the balloons 107A and 107B can detect a change and can cause an alarm to be generated or corrective action to be taken.

As shown in the example of FIG. 1, the balloon catheter 101 is disposed in a delivery sheath 140. In other implementations, the delivery sheath 140 is not included. In some implementations that have a delivery sheath, the delivery sheath 140 is a hollow tube that can be initially placed inside a patient and subsequently used as a conduit for other medical devices, such as the balloon catheter 101. For procedures in which several catheters may be employed (e.g., catheters of different sizes or having different characteristics or functions), the delivery sheath 140 can protect the patient's internal body organs and body lumens through which the various medical devices are navigated. In addition, the delivery sheath 140 can facilitate easier navigation of other medical devices, by a physician or other technician, to a treatment site.

The delivery sheath 140 may be steerable, and it may be characterized by a specific diameter, length, distal feature, etc. For example, delivery sheaths may be available in varying diameters, such as 8.5 Fr (French), 10 Fr, 11 Fr, etc.; varying lengths, such as 60 cm, 65 cm, 71 cm, 78 cm, 90 cm, etc.; and having distal ends that are biased in various shapes, such as, for example, in a 15° curve, a 55° curve, a short 120° curve, a long 120° curve, etc. Different delivery sheaths may be configured for different procedures. For example, a delivery sheath having one biased curvature may be particularly effective for guiding a cryo balloon to a patient's pulmonary veins to treat atrial fibrillation, while a delivery sheath having a different biased curvature may be particularly effective for another procedure, such as one in which a stent is delivered and positioned within a patient's vasculature.

In some implementations, as depicted in FIG. 1, a distal tip 145 of the delivery sheath 140 is slightly tapered, for example, to facilitate navigation of the tip 145 through a patient's vasculature, or to facilitate crossing of tissue membranes of the patient (e.g., the septal wall, during a procedure to treat atrial fibrillation). The proximal end 148 may be tapered to more easily receive other medical devices, such as the balloon catheter 101 that is shown disposed in the delivery sheath 140.

Exemplary cryotherapy catheters can include other components and structures that are not shown in FIG. 1. In particular, for example, a cryotherapy catheter may include one or more temperature sensors in the chamber 119, on or in the balloon 107, on the shaft 110, etc. A pressure sensing lumen can also be included to detect pressure inside the chamber 119, outside the balloon 107, between the balloons 107A and 107B, etc. Various electrodes can be included on the balloon 107 (e.g., to sense electrical activity in tissue to potentially be treated, or to stimulate electrical activity in such tissue). Other features are possible and contemplated.

As mentioned above, the balloon 107 can be configured in a number of ways to include the cooling region 108 and the thermally insulated region 109. In particular, the balloon 107 can include a number of different thermal profiling components disposed inside the interior chamber 119 or in the balloon 107 structure itself. A number of specific example thermal profiling components are now described.

Figure 2:
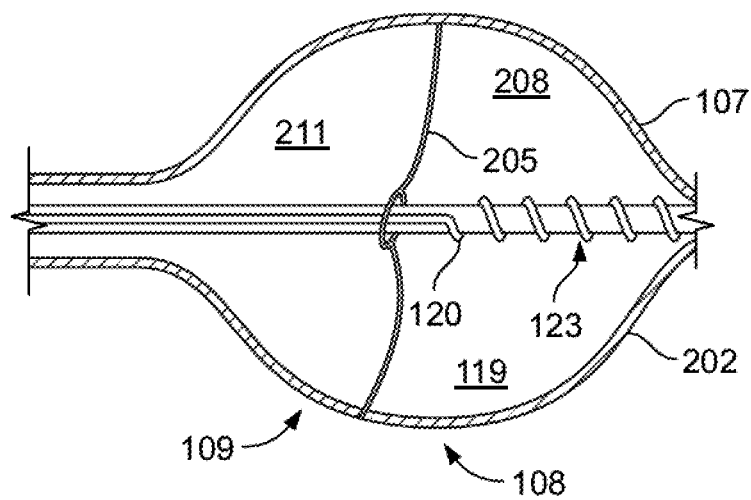
FIG. 2 illustrates an example thermal profiling component that can be disposed inside the cryo balloon shown in FIG. 1 to provide cooling and thermally insulated regions.

FIG. 2 illustrates one example thermal profiling component that can be disposed inside the cryo balloon 107, such that a cooling region 108 and a thermally insulated region 109 are provided on an external surface 202 of the balloon 107. In particular, FIG. 2 illustrates a diaphragm 205 that can be included inside the interior chamber 119. In some implementations, the diaphragm 205 is a membrane that can isolate in one portion 208 of the interior chamber 119 cryogenic agent that is released into the interior chamber 119. For example, in some implementations, the diaphragm 205 substantially isolates the cryogenic agent in a distal portion 208 of the interior chamber 119 from a proximal portion 211 of the interior chamber (e.g., the diaphragm may isolate 75%, 80%, 95%, 99%, etc., of the cryogenic agent in the distal portion 208). In such implementations, the corresponding cooling effect of the cryogenic agent can be focused on the distal cooling region 108, and air or another insulating material in the proximal portion 211 can insulate the thermally insulated region 109 from the cryogenic agent.

In some implementations, the diaphragm 205 is a breathable membrane that only partially separates the distal portion 208 from the proximal portion 211. For example, such a breathable membrane can substantially maintain cryogenic agent in liquid form in the distal portion 208, while allowing cryogenic agent in gaseous form to pass through. In such implementations, most (but not necessarily all) of the cooling effect corresponding to the cryogenic agent can be focused in the distal portion 208 corresponding to the cooling region 108. That is, much or substantially all (e.g., 75%, 80%, 95%, 99%, etc.), of a liquid cryogenic agent can flash to a gas in the distal portion 208, which can be bounded by the diaphragm 205. Since much of the heat that can be extracted by a liquid cryogenic agent flashing to a gas is extracted by the liquid-to-gas state change itself (rather than convection or conduction of heat to a cool resulting gas), much of the cooling effect is focused on the region in which the state change occurs (e.g., the distal portion 208). Some liquid cryogenic agent may cross the diaphragm, and accordingly, some cooling may occur in the proximal portion 211. In addition, some convection and conduction of heat to the gaseous cryogenic agent in the proximal portion 211 may also occur (as it does in the distal portion 208), resulting in some cooling of tissue adjacent to the thermally insulated region 109. However, in some implementations, the diaphragm 205 can focus much of the cooling effect of the cryogenic agent on the distal cooling region 108.

In some implementations, a breathable diaphragm may simplify construction of the balloon 107 relative to a non-breathable diaphragm. That is, providing a breathable diaphragm can enable gaseous cryogenic agent to be exhausted through an exhaust lumen in the proximal portion 211 in a manner that maintains the balloon 107 in an inflated state without additional lumens or balloon structures. In implementations in which a non-breathable diaphragm is employed, separate inflation and exhaust lumens may be included to separately inflate the proximal portion 211. Such implementations may include—in addition or in place of such additional lumens—splines or other structural members to maintain the proximal portion in an expanded (e.g., inflated) state.

In some implementations, the diaphragm 205 can serve another function, in addition to thermally insulating the proximal portion 211 from the cryogenic agent. In particular, the diaphragm 205 can be anchored to walls of the interior region 119 (e.g., to the inner walls of the inner balloon 107A in multi-balloon implementations) in a manner that enables the diaphragm 205 to help deflate the balloon 107. For example, the diaphragm 205 could apply a constant force in a radially inward direction that, absent a threshold pressure in the interior chamber 119, draws the walls of the balloon 107 inward, to a collapsed state.

In some implementations, the diaphragm 205 is movable within the interior chamber 119. For example, the diaphragm may be slideably translatable along a central lumen (e.g., with the addition of a control wire or other actuating member), such that the shape and relative size of the distal portion 208 and proximal portion 211 can be dynamically adjustable during a procedure. In such implementations, the relative size of the cooling region 108 and thermally insulated region 109 may be correspondingly adjustable.

Figure 3:
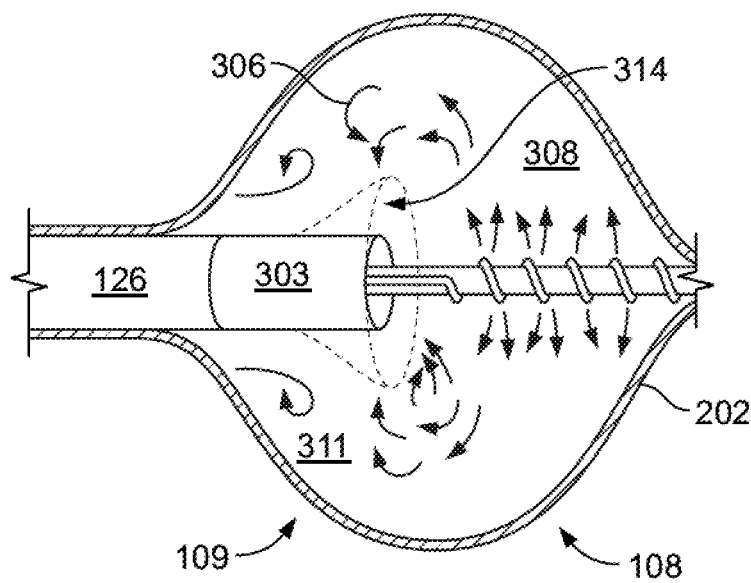
FIG. 3 illustrates another example thermal profiling component that can be disposed inside the cryo balloon shown in FIG. 1.

FIG. 3 illustrates another example thermal profiling component that can be disposed inside the cryo balloon 107 such that the cooling region 108 and the thermally insulated region 109 are provided on the external surface 202 of the balloon 107. In particular, an extension 303 to the exhaust lumen 126 can be provided, such that exhaust is drawn from a more central or distal region 308 of the interior chamber 119, rather than from a more proximal region 311. In some implementations, drawing exhaust from a more distal region 308 of the interior chamber 119 can create eddy currents 306 in the interior chamber 119 that tend to focus much of the flow of cryogenic agent in a distal region 308 of the interior chamber 119 and away from a proximal region 311 of the interior chamber 119. Focusing the flow of the cryogenic agent in this manner can focus the corresponding cooling effect on the distal portion 308 of the balloon.

The extent of the eddy currents 306 and of their corresponding ability to focus flow of cryogenic agent can depend on overall shape of the balloon 107, overall shape of the exhaust lumen 126 and of its opening 314, and longitudinal position of the opening 314 within the chamber 119. In some implementations, the opening 314 is flared open, or funnel shaped, at its distal end (e.g., to draw exhaust flow from an area that is larger than the cross-sectional area of the exhaust lumen 126 at points other than the opening). In other implementations, the opening 314 is narrowed (not shown in FIG.

3) relative to a cross-section of the exhaust lumen 126 at other points (e.g., to increase the velocity of the exhaust at the opening 314).

In different implementations, the extension 303 can have different lengths (that is, the opening 314 can have different longitudinal positions in different implementations), such that exhaust can be drawn from different points within the interior chamber 119. In some implementations, the longitudinal position of the opening 314 can be dynamically adjustable during a procedure. For example, a dedicated guidewire or other actuator can be employed to translate the extension 303 in order to longitudinally adjust the position of the opening 314. In some implementations, the size and shape of the opening 314 can also be dynamically adjustable. For example, a dedicated inflatable structure, guidewire or other actuator can be employed to flare or close the opening 314.

Figure 4A:
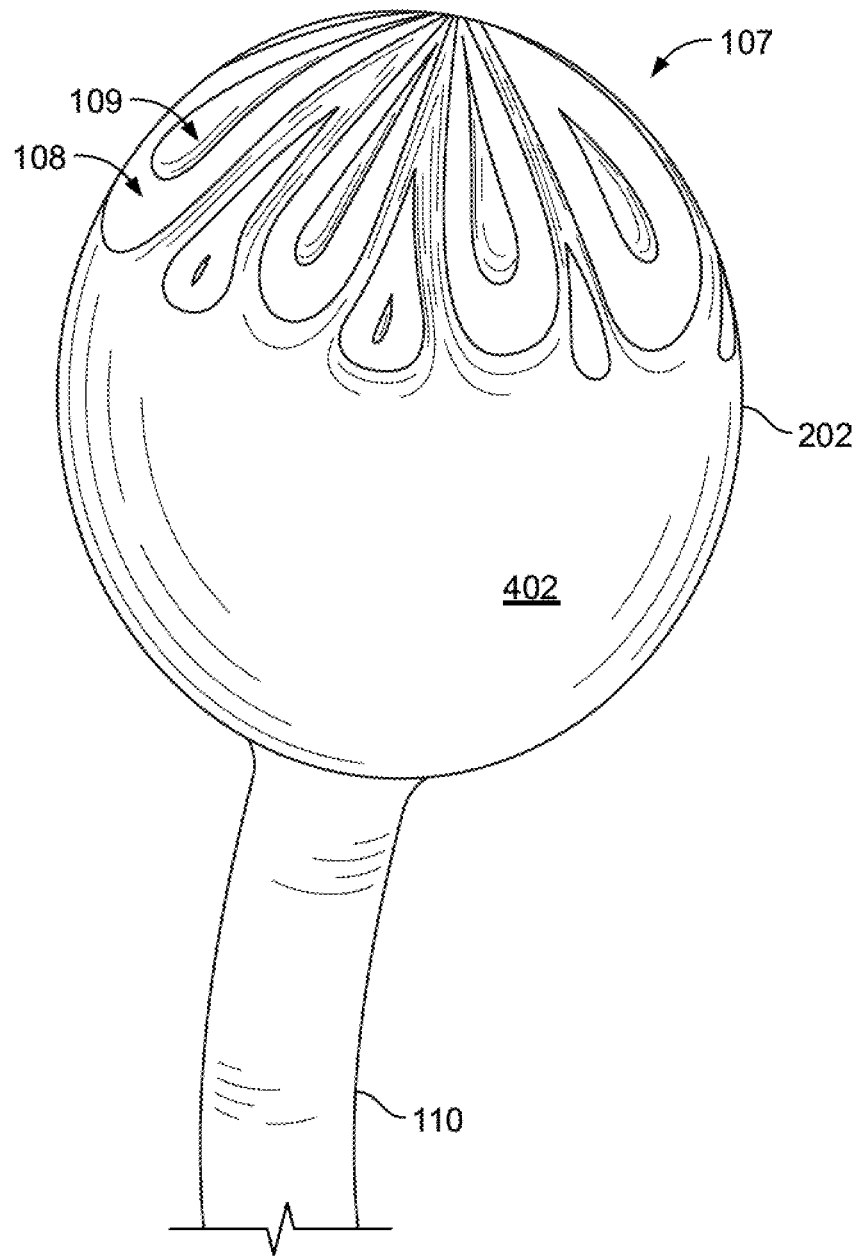
FIGS. 4A-4E illustrate other example thermal profiling components that can be disposed on or in the cryo balloon shown in FIG. 1.

FIGS. 4A-4E illustrate other example thermal profiling components that can be disposed on or in the cryo balloon 107 to provide a cooling region 108 and a thermally insulated region 109. In particular, FIG. 4A depicts an insulative material 402 (e.g., a material having a relatively low thermal conductivity) that can be employed to thermally insulate certain regions of the external surface 202 of the balloon 107 from the cryogenic agent and allow other regions of the external surface 202 to be thermally coupled to the cryogenic agent in the interior chamber 119. Various example insulative materials are depicted in and described in more detail with reference to FIGS. 4B-4E and 5A-5B.

As shown in one example in FIG. 4A, the insulative material 402 can be disposed in such a manner as to form a cooling region 108 in a treatment pattern shape which, during a cryotherapy procedure, can cause body tissue that is in contact with the treatment pattern shape to be cryoablated, without cryoablating body tissue that is not in contact with the treatment pattern shape (e.g., tissue that is in contact with the insulative material 402). In some implementations, the insulative material 402 is radio-opaque (e.g., to assist a technician in delivering cryotherapy).

Figures 7A, 7B:
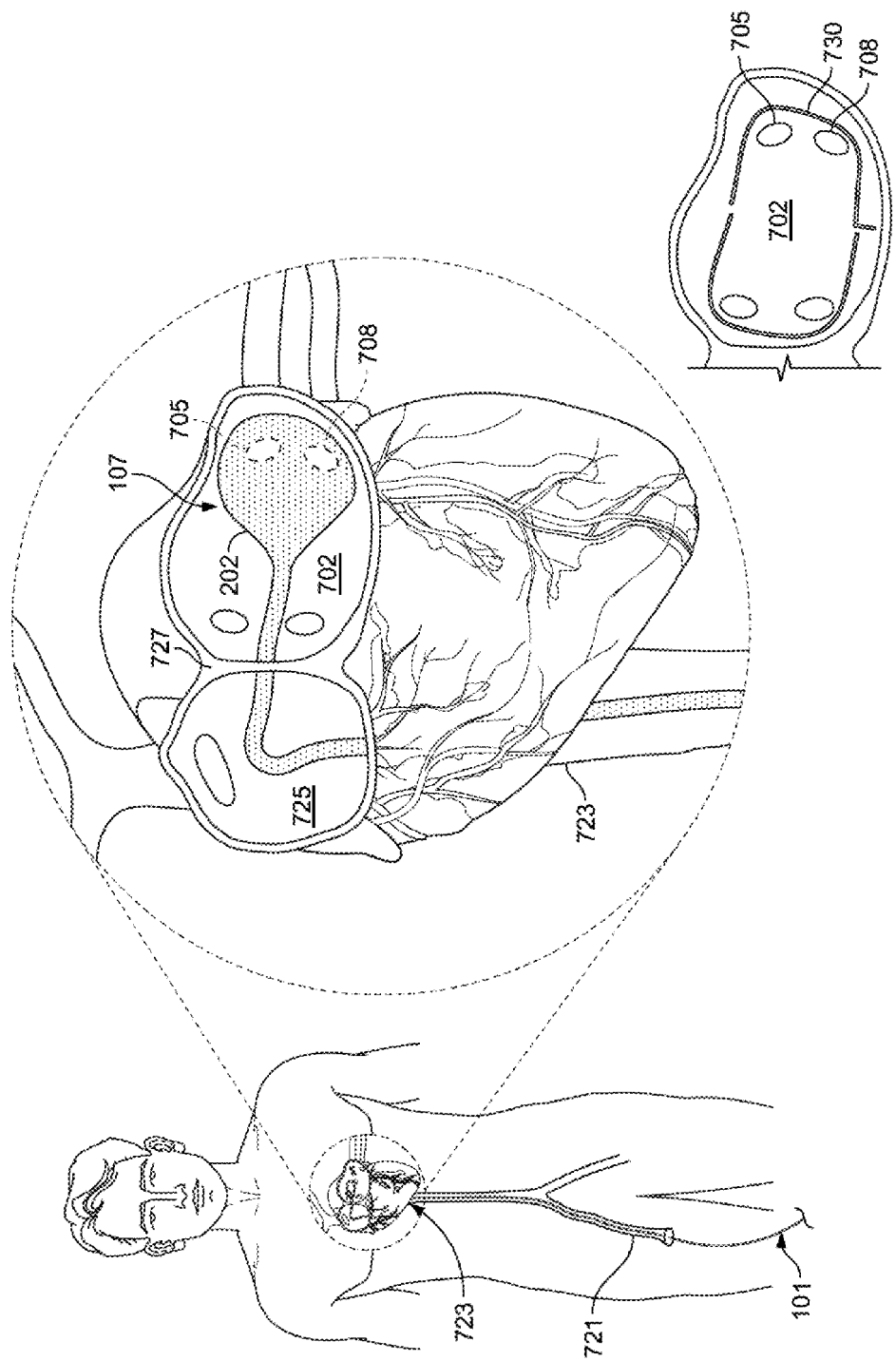
FIG. 7A illustrates, for anatomical reference, the balloon catheter of FIG. 1 disposed in patient's left atrium.
FIG. 7B illustrates, for anatomical reference, a region within the patient's left atrium shown in FIG. 7A that may be ablated during a cryotherapy procedure.

In some implementations, the treatment pattern shape corresponds to at least a portion of a Maze pattern, an example of which is shown for reference in FIGS. 7A and 7B. With reference to FIG. 7A, the balloon 107 can be configured to be inflated inside a patient's left atrium 702 in a manner in which the external surface 202 of the balloon 107 contacts multiple pulmonary vein ostia (e.g., the left superior pulmonary vein 705 and left inferior pulmonary vein 708). The treatment pattern shape can be configured to ablate tissue around multiple corresponding ostia (e.g., in a pattern corresponding to at least a portion of the ablation pattern 730 shown in FIG. 7B). In this example, the inflated balloon 107 can be relatively large (e.g., 10 cm or more in diameter). For purposes of example, the inflated balloon 107 in FIG. 7A is depicted as covering the ostia of two pulmonary veins, although a balloon inflated to close to 10 cm may in fact cover three or four ostia of a patient's pulmonary veins. In other implementations, the inflated balloon 107 can be smaller (e.g., 3 cm in diameter or smaller) and can be configured to ablate the ostium of one pulmonary vein at a time. In still other implementations, the balloon 107 can be between 3 cm and 10 cm when inflated, or the balloon 107 can have other dimensions when inflated. In some implementations, the treatment pattern may have a different shape, such as one including one or more linear segments, a circumferential segment, a corkscrew shape, a series of adjacent segments or dots, or a segment or segments having other shapes. Moreover, the balloon itself can have various shapes when inflated (e.g., the balloon can be spherically shaped, pear-shaped, shaped to correspond to particular anatomy of a patient, etc.).

For additional reference, FIG. 7A illustrates one example path through which the catheter 101 can be routed inside a patient body, to the patient's left atrium. Specifically, the catheter 101 can be routed through the patient's femoral vein 721, into the inferior vena cava 723 and right atrium 725, through the septal wall 727, and into the left atrium 702. This path is merely exemplary, and the reader will appreciate that the concepts described herein can be applied to catheters that may be routed through other paths and/or employed in various other procedures.

Referring again to FIGS. 1-4A, the balloon 107 itself can be formed from a polymer including, but not limited to, polyolefin copolymer, polyester, polyethylene teraphthalate, polyethylene, polyether-block-amide, polyamide (e.g., nylon), polyimide, latex, a urethane-family material, neoprene, etc. In particular, for example, certain implementations of the balloon 107 include PEBAX® 7033 material (70D poly ether amide block). Other suitable resins, plastics or polymers can also be employed.

In some implementations, the balloon 107 can be constructed by blow-molding a polymer extrusion into the desired shape. In other implementations, the balloon 107 can be constructed by dipping a mandrel in an appropriate liquid material, and allowing the material to cure. In some implementations, the balloon 107 can be constructed to expand to a desired shape when pressurized without elastically deforming substantially beyond the desired shape.

A number of ancillary processes may be used to affect the material properties of the balloon 107. For example, the polymer extrusion may be exposed to gamma radiation which can alter the polymer infrastructure to provide uniform expansion during blow molding and additional burst strength when in use. In addition, the formed balloon 107 may be exposed to a low temperature plasma field which can alter the surface properties to provide enhanced adhesion characteristics. Other materials and manufacturing processes can be used to provide the balloon 107 with desired characteristics. Some example processes for insulating portions of the balloon 107 are now described with reference to FIGS. 4B-4E and 5A-5B.

Figure 4B:
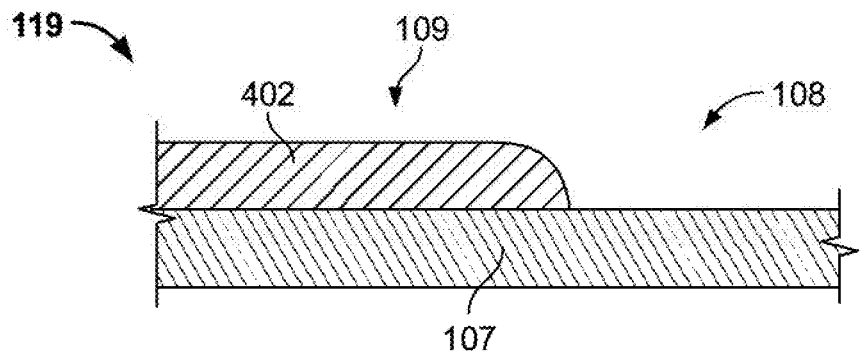

FIG. 4B illustrates one example method of providing an insulative material 402 in which the insulative material is disposed at locations corresponding to the thermally insulated regions 109, on the outside of the balloon 107. The insulative material 402 can be any appropriate biocompatible material having thermally insulative properties, and the insulative material 402 can be disposed on the balloon 107 in various manners. For example, in some implementations, a balloon 107 can be inflated and dipped in a thermally insulative material 402. In other implementations, the thermally insulative material can be formed separately from the balloon 107, and then subsequently laminated on the balloon 107 in any appropriate pattern. The material of the balloon 107 itself can be a relatively more thermally conductive material than the insulative material 402.

Figure 4C:
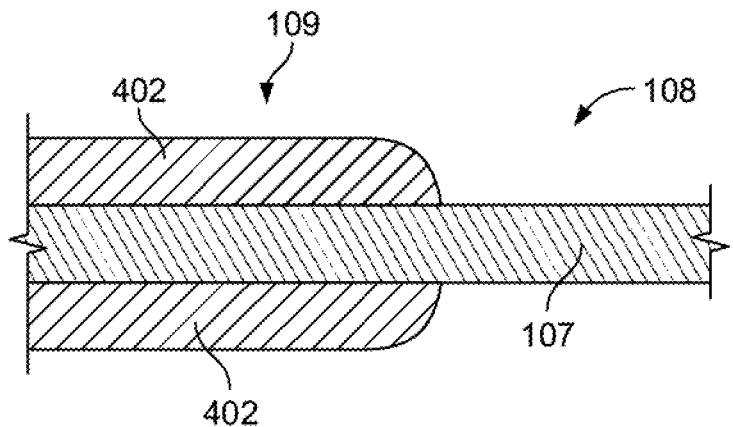

In the example depicted in FIG. 4B, the insulative material 402 is disposed on the outside of the balloon 107, but the reader will appreciate that the insulative material could also be disposed on the inside of the balloon 107. In some implementations, the insulative material is disposed on both the inside and outside of the balloon 107, as depicted in FIG. 4C. In such implementations, the balloon 107 and insulation may be, for example, co-extruded. As another example, the balloon 107 shown in FIG. 4C may be progressively formed, for example, by dipping a mandrel in liquid insulative material, allowing the insulative material to at least partially cure, dipping the mandrel and insulative material in liquid balloon material, allowing the balloon material to at least partially cure, dipping the mandrel/insulative material/balloon material into an insulative material, etc. Appropriate masking can be employed between layers to form the insulative material as desired. In some implementations, multiple layers of insulative material 402 can be disposed on a balloon, such that they are not completely overlapping—for example, to form a stepped pattern that provides multiple gradations of thermal insulation.

Multiple balloon layers can be formed in various other ways. For example, balloons or balloon layers can be separately formed and glued, melted, or laser-welded together. Or, multi-layer balloons can be formed or molded as one piece, in a single process. The above are merely examples. The reader will appreciate that multi-layer balloons can be formed with any appropriate balloon-forming method. In multi-balloon implementations, the insulative material can be disposed between an inner balloon 107A and an outer balloon 107B, as depicted in FIG. 4D.

Figure 4D:
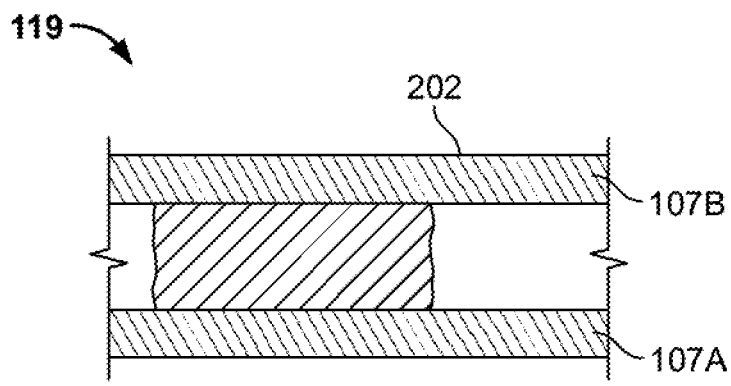
Figure 4E:
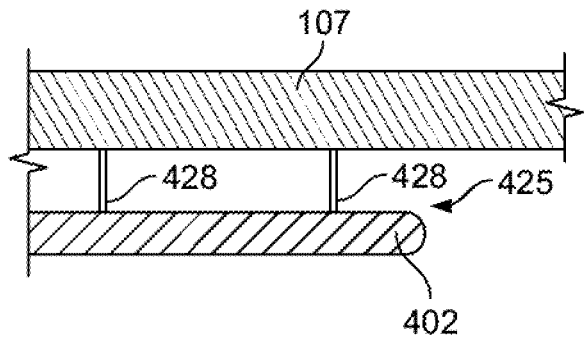

In the examples of FIG. 4B-4D, the insulative material is shown to be in contact with the surface of the balloon 107. In other implementations, such as the one depicted in FIG. 4E, an air gap 425 can be disposed between a wall of the balloon 107 and the insulative material 402, and the air gap 425 can provide additional insulation. In some implementations that include an air gap, posts or other spacers 428 can be employed to maintain a separation between the walls of the balloon 107 and the insulative material.

Figure 5A:
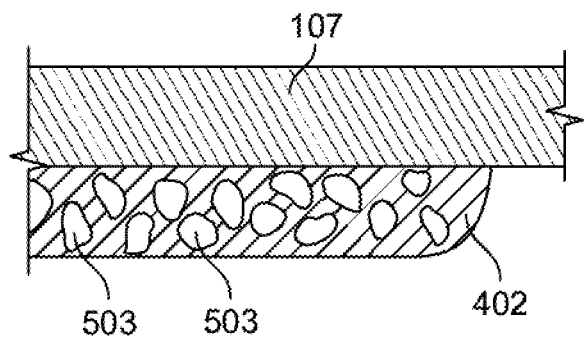
FIGS. 5A and 5B illustrate additional details of example insulative material that can be employed in the implementations depicted in FIGS. 4A-4E.
Figure 5B:
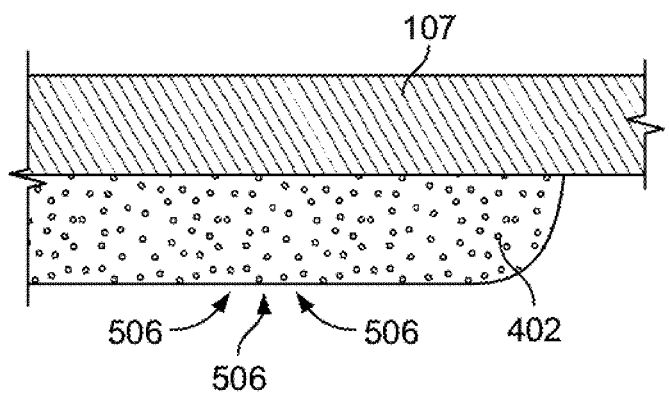

FIGS. 5A and 5B illustrate additional details of example insulative material 402 that can be employed in implementations such as those depicted in FIGS. 4A-4E. In some implementations, the insulative material is formed from the same material as the balloon 107 (e.g., PEBAX®), and the insulative material employs air pockets 503 trapped within the material to provide or supplement insulative properties, as shown in FIG. 5A. In other implementations, hollow beads 506 (e.g., glass beads, or beads constructed from another appropriate material) can be disposed in the insulative material 402 (e.g., PEBAX®, latex, urethane, or another suitable material) to provide or supplement insulative properties.

Figure 6:
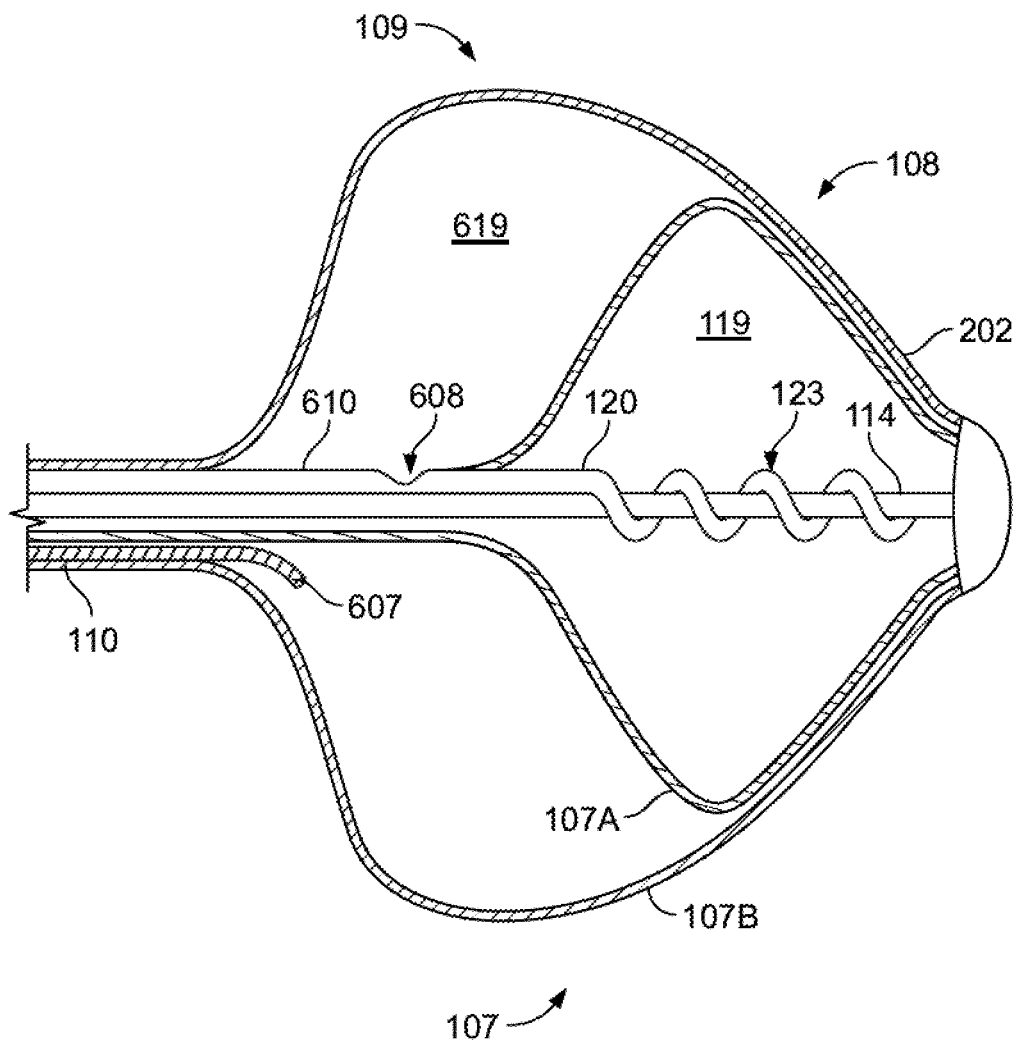
FIG. 6 illustrates another example implementation in which cooling and thermally insulated regions can be provided in a cryo balloon.

FIG. 6 illustrates another example implementation in which an internal balloon 107A can be disposed inside a safety balloon 107B to provide thermal isolation to provide a separate cooling region 108 and thermally insulated region 109. In particular, as shown, the internal balloon 107A can be configured to have a smaller size than the external safety balloon 107B. During a cryotherapy procedure, both the internal balloon 107A and safety balloon 107B can be inflated (e.g., the safety balloon 107B can be inflated to help anchor the balloon portion 107 at a treatment site internal to a patient's body).

In some implementations, the safety balloon 107B can be inflated with a separate supply line 607. In some implementations, a channel 608 in a shaft 610 inside the safety balloon 107B can fluidly couple the interior chamber 119 and an insulative chamber 619 between the inner balloon 107A and the safety balloon 107B, such that the safety balloon 107B is inflated by a cryogenic agent that is released into the inner balloon 107A. In such implementations, the channel 608 can function in a similar manner as the diaphragm 205 that is depicted in and described with reference to FIG. 2. That is, the channel 608 can, in some implementations, allow gaseous cryogenic agent to enter region 619, but substantially isolate liquid cryogenic agent from the region 619—resulting in the region 619 (and thus the region 109 on the surface 202 of the balloon 107B) being substantially thermally insulated from the cooling effect of the cryogenic agent in the inner balloon 107A.

A number of implementations have been described. Nevertheless, it will be understood that various modifications may be made without departing from the spirit and scope of this document. In particular, for example, cryotherapy balloon catheters are described as employing the Joule-Thomson effect to cool using a liquid-to-gas phase change, but liquid-based cryocatheters can also include cooling regions and thermally insulated regions. Moreover, cryotherapy catheters can be employed to deliver targeted cryotherapy to regions of a patient's body other than the patient's heart (including, for example, a patient's prostate gland, or other glands; a portion of the patient's gastro-intestinal tract; a small (e.g., varicose) vein; or other suitable internal treatment sites). Multiple cooling and thermally insulating regions can be provided, and the regions can be formed in various shapes and sizes. Accordingly, other implementations are within the scope of the following claims.

What is claimed is:

1. A cryotherapy catheter comprising:
an elongate member and an inflatable balloon portion at a distal end of the elongate member, the inflatable balloon portion having an external surface and an interior chamber and comprising an inner balloon and an outer balloon; the external surface comprising a cooling region and a thermally insulated region; the interior chamber configured to receive during a cryotherapy procedure a cryogenic agent for extracting heat from body tissue that is in contact with the cooling region; and
an insulative material disposed between the inner balloon and the outer balloon, or adjacent to a surface of at least one of the inner balloon or the outer balloon; the insulative material comprising a material having at least one of a plurality of air pockets formed therein or a plurality of hollow beads disposed therein;
wherein the insulative material is disposed in a manner that thermally insulates the thermally insulated region from the cryogenic agent to minimize heat extraction by the cryogenic agent from body tissue that is in contact with the thermally insulated region.

2. The cryotherapy catheter of claim 1, wherein inner insulative material is disposed adjacent to a surface of the inner balloon, and an air gap is disposed between the inner insulative material and the surface of the inner balloon.

3. The cryotherapy catheter of claim 1, wherein the insulative material is disposed in multiple non-overlapping layers and configured to provide multiple gradations of thermal insulation.

4. The cryotherapy catheter of claim 1, wherein the insulative material is configured to form the cooling region in a treatment pattern shape which, during the cryotherapy procedure, causes body tissue that is adjacent to the treatment pattern shape to be cryoablated, without cryoablating body tissue that is not in contact with the treatment pattern shape.

5. The cryotherapy catheter of claim 4, wherein the treatment pattern shape is configured to correspond to at least a part of a Maze-Cox pattern.

6. The cryotherapy catheter of claim 4, wherein the treatment pattern shape is configured to thermally insulate bodily tissue or fluids that are in contact with a proximal end of the inflatable balloon portion during the cryotherapy procedure from a cooling effect of the cryogenic agent.

* * * * *